United States Patent
Mazor et al.

(10) Patent No.: US 9,606,073 B2
(45) Date of Patent: Mar. 28, 2017

(54) X-RAY SCATTEROMETRY APPARATUS

(71) Applicant: JORDAN VALLEY SEMICONDUCTORS LTD., Migdal HaEmek (IL)

(72) Inventors: Isaac Mazor, Haifa (IL); Alex Krokhmal, Haifa (IL); Alex Dikopoltsev, Haifa (IL); Matthew Wormington, Littleton, CO (US)

(73) Assignee: BRUKER JV ISRAEL LTD., Migdal Haemek (IL)

( * ) Notice: Subject to any disclaimer, the term of this patent is extended or adjusted under 35 U.S.C. 154(b) by 0 days.

(21) Appl. No.: 14/735,162

(22) Filed: Jun. 10, 2015

(65) Prior Publication Data

US 2015/0369759 A1   Dec. 24, 2015

Related U.S. Application Data

(60) Provisional application No. 62/015,451, filed on Jun. 22, 2014.

(51) Int. Cl.
  *G01N 23/201* (2006.01)
(52) U.S. Cl.
  CPC ... *G01N 23/201* (2013.01); *G01N 2223/6116* (2013.01)
(58) Field of Classification Search
  USPC .......................................................... 378/90
  See application file for complete search history.

(56) References Cited

U.S. PATENT DOCUMENTS

| | | | |
|---|---|---|---|
| 4,989,226 A | 1/1991 | Woodbury et al. | |
| 5,481,109 A | 1/1996 | Ninomiya et al. | |
| 5,619,548 A | 4/1997 | Koppel | |
| 5,740,226 A | 4/1998 | Komiya et al. | |
| 5,900,645 A | 5/1999 | Yamada | |
| 6,041,098 A | 3/2000 | Touryanski et al. | |
| 6,163,592 A * | 12/2000 | He | G01N 23/20 378/70 |

(Continued)

OTHER PUBLICATIONS

Jones et al., "Small angle x-ray scattering for sub-100 nm pattern characterization", Applied Physics Letters, vol. 83, No. 19, pp. 4059-4061, Nov. 10, 2003.

(Continued)

*Primary Examiner* — Phillip A Johnston
(74) *Attorney, Agent, or Firm* — D. Kligler IP Services Ltd.

(57) ABSTRACT

Apparatus, including a sample-support that retains a sample in a plane having an axis, the plane defining first and second regions separated by the plane. A source-mount in the first region rotates about the axis, and an X-ray source on the source-mount directs first and second incident beams of X-rays to impinge on the sample at first and second angles along beam axes that are orthogonal to the axis. A detector-mount in the second region moves in a plane orthogonal to the axis and an X-ray detector on the detector-mount receives first and second diffracted beams of X-rays transmitted through the sample in response to the first and second incident beams, and outputs first and second signals, respectively, in response to the received first and second diffracted beams. A processor analyzes the first and the second signals so as to determine a profile of a surface of the sample.

20 Claims, 7 Drawing Sheets

(56) References Cited

U.S. PATENT DOCUMENTS

| | | | |
|---|---|---|---|
| 6,226,349 B1 | 5/2001 | Schuster et al. | |
| 6,242,745 B1 * | 6/2001 | Berlad | G01T 1/1642 |
| | | | 250/370.01 |
| 6,271,534 B1 * | 8/2001 | Kumakhov | G01N 23/04 |
| | | | 250/505.1 |
| 6,381,303 B1 | 4/2002 | Vu et al. | |
| 6,389,102 B2 | 5/2002 | Mazor et al. | |
| 6,512,814 B2 | 1/2003 | Yokhin et al. | |
| 6,556,652 B1 | 4/2003 | Mazor et al. | |
| 6,639,968 B2 | 10/2003 | Yokhin et al. | |
| 6,680,996 B2 | 1/2004 | Yokhin et al. | |
| 6,750,952 B2 | 6/2004 | Grodnensky et al. | |
| 6,754,304 B1 | 6/2004 | Kumakhuv | |
| 6,754,305 B1 | 6/2004 | Rosencwaig et al. | |
| 6,810,105 B2 | 10/2004 | Nasser-Ghodsi et al. | |
| 6,859,520 B2 * | 2/2005 | He | G01N 23/20016 |
| | | | 378/71 |
| 6,879,051 B1 | 4/2005 | Singh et al. | |
| 7,076,024 B2 | 7/2006 | Yokhin | |
| 7,110,491 B2 | 9/2006 | Mazor et al. | |
| 7,120,228 B2 | 10/2006 | Yokhin et al. | |
| 7,483,513 B2 | 1/2009 | Mazor et al. | |
| 7,551,719 B2 * | 6/2009 | Yokhin | G01N 23/20008 |
| | | | 378/70 |
| 8,437,450 B2 | 5/2013 | Wall et al. | |
| 8,687,766 B2 | 4/2014 | Wormington et al. | |
| 2001/0043668 A1 | 11/2001 | Hayashi et al. | |
| 2003/0128809 A1 | 7/2003 | Umezawa et al. | |
| 2004/0156474 A1 | 8/2004 | Yokhin et al. | |

OTHER PUBLICATIONS

Jones et al., "3-Dimensional Lineshape Metrology Using Small Angle X-ray Scattering", AIP Conference Proceedings, vol. 683, Issue 1, 4 pages, Sep. 2003.

Wormington et al., "Characterization of structures from X-ray scattering data using genetic algorithms", The Royal Society, Philosophical Transactions: Mathematical, Physical and Engineering Sciences, vol. 357, No. 1761, X-Ray Topography and Crystal Characterization, pp. 2827-2848, Oct. 15, 1999.

Axo Dresden GmbH, "Applied X-ray Optics and High Precision Deposition", Technical Data Sheet, 23 pages, May 22, 2013.

DECTRIS LTD.,—detecting the future, Eiger X, Detector Series, "The Summit of Hybrid Photon Counting", 4 pages, Sep. 9, 2015.

OXFORD Instruments., "50kV Microfocus X-ray source", Technical Data Sheet, 2 pages, May 19, 2015.

KENOCS., "X-ray earn delivery system", Technical Data Sheet, 4 pages, Sep. 15, 2009.

XOS., "Polycapillary Optics for Micro X-Ray Fluorescence and X-Ray Diffraction ", 4 pages, Jul. 23, 2015.

Jones et al., "Subnanometer wavelength metrology of lithographically prepraed structures: a comparison of neutron and X-ray scattering", Proceedings of the SPIE, vol. 5038, pp. 191-199, 2003.

Wiener et al., "Characterization of Titanium Nitride Layers by Grazing—Emission X-Ray Fluorescence Spectrometry", Applied Surface Science, vol. 125, pp. 129-136, Elsevier Science B.V., year 1999.

Oxford Instruments Inc., X-ray Tube Information, Series 5000, Model XTF5011, "Packaged X-Ray tubes", Technical Data Sheet, 3 pages, Jun. 1998.

Hayashi et al., "Refracted X-Rays Propagating Near the Surface Under Grazing Incidence Condition", Spectrochimica Acta, Part B 54, pp. 227-230, year 1999.

X-Ray Optical Systems, Inc., "Monolithic Polycapillary Lens Information", Albany, USA, 1 page, Dec. 29, 1998.

Di-Fonzo et al., "Non-Destructive Determination of Local Strain with 100—Nanometre Spatial Resolution", Letters to Nature, vol. 403, pp. 638-640, Feb. 10, 2000.

Guerault, "Specular Reflectivity and Off—Specular Scattering: Tools for Roughness Investigation", Institute Voor Kern-en Stralingsfysica, 15 pages, Dec. 15, 2000.

Hu et al., "Small Angle X-Ray Scattering Metrology for Sidewall Angle and Cross Section of Nanometer Scale Line Gratings", Journal of Applied Physics, vol. 96, No. 4, pp. 1983-1987, Aug. 15, 2004.

Wu et al., "Small Angle Neutron Scattering Measurements of Nanoscale Lithographic Features", Polymer Preprints, vol. 42, No. 1, pp. 265-266, year 2001.

Kojima et al., "Structural Characterization of Thin Films by X-Ray Reflectivity", Rigaku Journal, vol. 16, No. 2, pp. 31-41, year 1999.

* cited by examiner

X-RAY SCATTEROMETRY APPARATUS

CROSS-REFERENCE TO RELATED APPLICATIONS

This application claims the benefit of U.S. Provisional Patent Application 62/015,451, filed Jun. 22, 2014, whose disclosure is incorporated herein by reference.

FIELD OF THE INVENTION

The present invention relates generally to X-ray metrology, and particularly to X-ray metrology of small structures.

BACKGROUND OF THE INVENTION

The accurate measurement of the shape and spatial dimensions (size) of small features is vitally important in the semiconductor industry. As the critical dimensions (CDs), such as feature width, shrink towards well below 100 nm, to 10 nm and below, traditional methods of measuring the key parameters required for manufacturing process control are becoming seriously challenged. These techniques include optical scatterometry, also known as optical critical dimension (OCD) metrology, which measures the shape and size of a feature through changes in the amplitude, intensity, and/or polarization of light generally in the infrared (IR) to ultra-violet (UV) range when scattered from a periodic array of the features. Another technique for dimensional analysis is scanning electron microscopy (SEM) and in particular the CD-SEM, which forms a top-down image of the features within the scanning area and can thus provide cross-sectional dimensions of individual features. These two techniques are the most widely used approaches to dimensional analysis in semiconductor manufacturing today.

As the semiconductor industry moves to ever smaller features and high aspect ratio (HAR) features, even the most advanced OCD and CD-SEM tools have issues due both to the small in-plane dimensions of the features to be measured and also to the relative depth of these features. In the case of OCD techniques with small features having such high aspect ratio, there are problems associated with getting the comparatively long-wavelength light into and out of the structures, whereas with CD-SEM only the top of the feature is probed and no information at significant depths is provided.

Other techniques such as atomic force microscopes (AFMs) have also been introduced to provide dimensional analysis of small individual features, but these suffer from not being able to insert the probe tip into the features of interest.

X-ray techniques have also been developed for dimensional analysis, and aspects of some of these are described below.

U.S. Pat. No. 6,680,996 to Yokhin, et al., whose disclosure is incorporated herein by reference, describes a method for testing a surface of a sample. The method includes finding respective first and second critical angles for total external reflection of radiation from an area of the surface at first and second wavelengths.

U.S. Pat. No. 7,110,491 to Mazor, et al., whose disclosure is incorporated herein by reference, describes a method of directing a beam of X-rays to impinge on an area of a periodic feature on a surface of a sample. The X-rays scattered from the surface in a reflection mode are used to detect a spectrum of diffraction in the scattered X-rays as a function of azimuth. The spectrum of diffraction is analyzed in order to determine a dimension of the feature.

U.S. Pat. No. 7,551,719 to Yokhin, et al., whose disclosure is incorporated herein by reference, describes apparatus for analysis of a sample. The apparatus includes a radiation source, which is adapted to direct a first, converging beam of X-rays toward a surface of the sample and to direct a second, collimated beam of the X-rays toward the surface of the sample. A motion assembly moves the radiation source between a first source position, in which the X-rays are directed toward the surface of the sample at a grazing angle, and a second source position, in which the X-rays are directed toward the surface in a vicinity of a Bragg angle of the sample.

Work on X-ray based CD measurements is described by Jones et al., in "Small Angle X-ray Scattering for Sub-100 nm Pattern Characterization," Applied Physics Letters 83:19 (2003), pages 4059-4061, which is incorporated herein by reference. The authors use transmission-mode small angle X-ray scattering (SAXS) with a synchrotron X-ray source to characterize a series of polymer photoresist gratings formed on a substrate. The X-ray beam passes through the grating and the substrate, and the SAXS pattern is measured using a two-dimensional CCD detector.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including:

a sample-support, configured to fixedly retain a sample in a plane having an axis, the plane defining first and second regions in space that are separated by the plane;

a source-mount, positioned in the first region, and configured to rotate about the axis;

an X-ray source positioned in the first region on the source-mount and configured to direct first and second incident beams of X-rays to impinge on the sample at respective first and second angles along respective beam axes that are orthogonal to the axis;

a detector-mount positioned in the second region and configured to move in a plane orthogonal to the axis;

an X-ray detector positioned in the second region on the detector-mount and configured to receive first and second diffracted beams of X-rays transmitted through the sample in response to the first and second incident beams, and to output first and second signals, respectively, in response to the received first and second diffracted beams; and a processor, configured to analyze the first and the second signals so as to determine a profile of a surface of the sample.

In a disclosed embodiment the X-ray source includes a single X-ray source configured to produce the first and second incident beams simultaneously.

In an alternative disclosed embodiment the X-ray source includes a first X-ray source configured to produce the first incident beam and a second X-ray source configured to produce the second incident beam simultaneously with the first incident beam.

In a further alternative disclosed embodiment the X-ray source includes a single X-ray source configured to produce the first and second incident beams sequentially.

The X-ray detector may consist of a first detector located at a first position on the detector-mount so as to receive the first diffracted beam and a second detector located at a second position on the detector-mount so as to receive the second diffracted beam.

In an alternative embodiment the detector-mount is configured to move so as to maintain alignment of the X-ray detector with the first and second diffracted beams on rotation of the source-mount about the axis. Typically, the detector-mount is configured to rotate about the axis.

In a further alternative embodiment the processor is configured to formulate an expected first signal and an expected second signal for the X-ray detector in response to a theoretical profile of the surface, and to compare, using a cost function, the expected first and second signals with the outputted first and second signals so as to determine the profile. The processor may be configured to minimize a sum of a first result of the cost function applied to the outputted first signal and the expected first signal and a second result of the cost function applied to the outputted second signal and the expected second signal so as to determine the profile.

The plane may be horizontal in which case the first region may be below the sample, and the second region may be above the sample.

There is further provided, according to an embodiment of the present invention a method, including:

configuring a sample-support to fixedly retain a sample in a plane having an axis, the plane defining first and second regions in space that are separated by the plane;

positioning a source-mount, configured to rotate about the axis, in the first region;

positioning an X-ray source in the first region on the source-mount;

directing first and second incident beams of X-rays from the X-ray source to impinge on the sample at respective first and second angles along respective beam axes that are orthogonal to the axis;

positioning a detector-mount, configured to move in a plane orthogonal to the axis, in the second region;

positioning an X-ray detector, configured to receive first and second diffracted beams of X-rays transmitted through the sample in response to the first and second incident beams, in the second region on the detector-mount;

outputting first and second signals, respectively, in response to the received first and second diffracted beams; and analyzing the first and the second signals so as to determine a profile of a surface of the sample.

The present invention will be more fully understood from the following detailed description of the embodiments thereof, taken together with the drawings in which:

DETAILED DESCRIPTION OF EMBODIMENTS

Overview

X-ray scatterometry, which is also known as critical dimension small-angle X-ray scattering (CD-SAXS) or just X-ray critical dimension (XCD) metrology, is a technique that has been demonstrated to be able to measure the cross sectional shape of small, high aspect ratio (HAR) features arranged in a periodic array.

In X-ray scatterometry, a beam of X-rays illuminates a periodic array of the features of a sample target whose dimensions are to be measured. The target causes the incident X-rays to be scattered over a few degrees of angular range with respect to the incident beam direction as a consequence of the periodicity and size being only several times the wavelength of the X-rays (~0.1 nm). The scattering may be observed as a series of peaks in the scattered intensity, whose position and separation are inversely proportional to a period of the periodic structure. The intensities of these peaks depend on the shape of the scattering features and therefore provide a means of determining the shape and size of the features.

Embodiments of the present invention provide an X-ray scatterometry system that uses transmission geometry. In transmission geometry, the X-rays are incident on one side of the sample and are transmitted through the sample, and then the scattered X-rays are measured on the opposite side. Since the X-rays penetrate the entire sample depth, around 700 μm in the case of a 300 mm Si wafer used in semiconductor manufacturing, there is no issue with getting the radiation in/out of the features of interest. Also, since the incident beam is typically close to normal to the surface of the sample, or within a few degrees of the normal, problems of significant X-ray spot elongation are not present, unlike small angle X-ray scatterometry in a reflection geometry.

In an embodiment of the present invention a sample-support is configured to fixedly retain a sample to be analyzed in a plane. The plane may be in any convenient orientation, including vertical, horizontal, or an orientation between vertical and horizontal. The plane also comprises an axis, which is referred to below. As for the plane of the sample, the axis within the plane may be in any convenient orientation, i.e., vertical, horizontal, or an orientation between vertical and horizontal. For simplicity in the following description, the plane and the axis are both assumed to be horizontal, and those having ordinary skill in the art will be able to adapt the description for other orientations of the plane and/or axis.

The plane defines two regions in space, a region above the plane and a region below the plane.

A source-mount is positioned in one of the regions defined by the plane, typically below the plane, and is configured to rotate about the horizontal axis. An X-ray source, in some embodiments two separate sources, is positioned on the source-mount, and is configured to direct first and second incident beams of X-rays to impinge on the sample at respective first and second angles along respective beam axes that are orthogonal to the horizontal axis.

A detector-mount is positioned in the other region defined by the plane. The detector-mount is configured to move in a plane orthogonal to the horizontal axis, and in some embodiments may be configured to rotate about the axis. An X-ray detector, typically two separate detectors, is positioned on the detector-mount, and is configured to receive first and second diffracted beams of X-rays transmitted through the sample in response to the first and second incident beams. The detector outputs first and second signals, respectively, in response to the received first and second diffracted beams. By having the detector-mount movable, the system is able to maintain the detectors in alignment with the diffracted beams regardless of rotation of the X-ray source on its source-mount.

A processor analyzes the first and second signals, typically by minimizing a cost function which compares the actual first and second signals with expected signals, to determine a profile of a surface of the sample.

By having a system which uses two separate X-ray incident beams, typically operated simultaneously, the efficiency of determination of the sample profile surface improves. In addition, by having both the X-ray source and the detectors able to rotate and/or move with respect to the fixed sample, multiple readings of the sample may be quickly effected, improving the accuracy of the profile determination, as well as extending the effective range of measurements on samples with HAR features.

System Description

Figure 1:
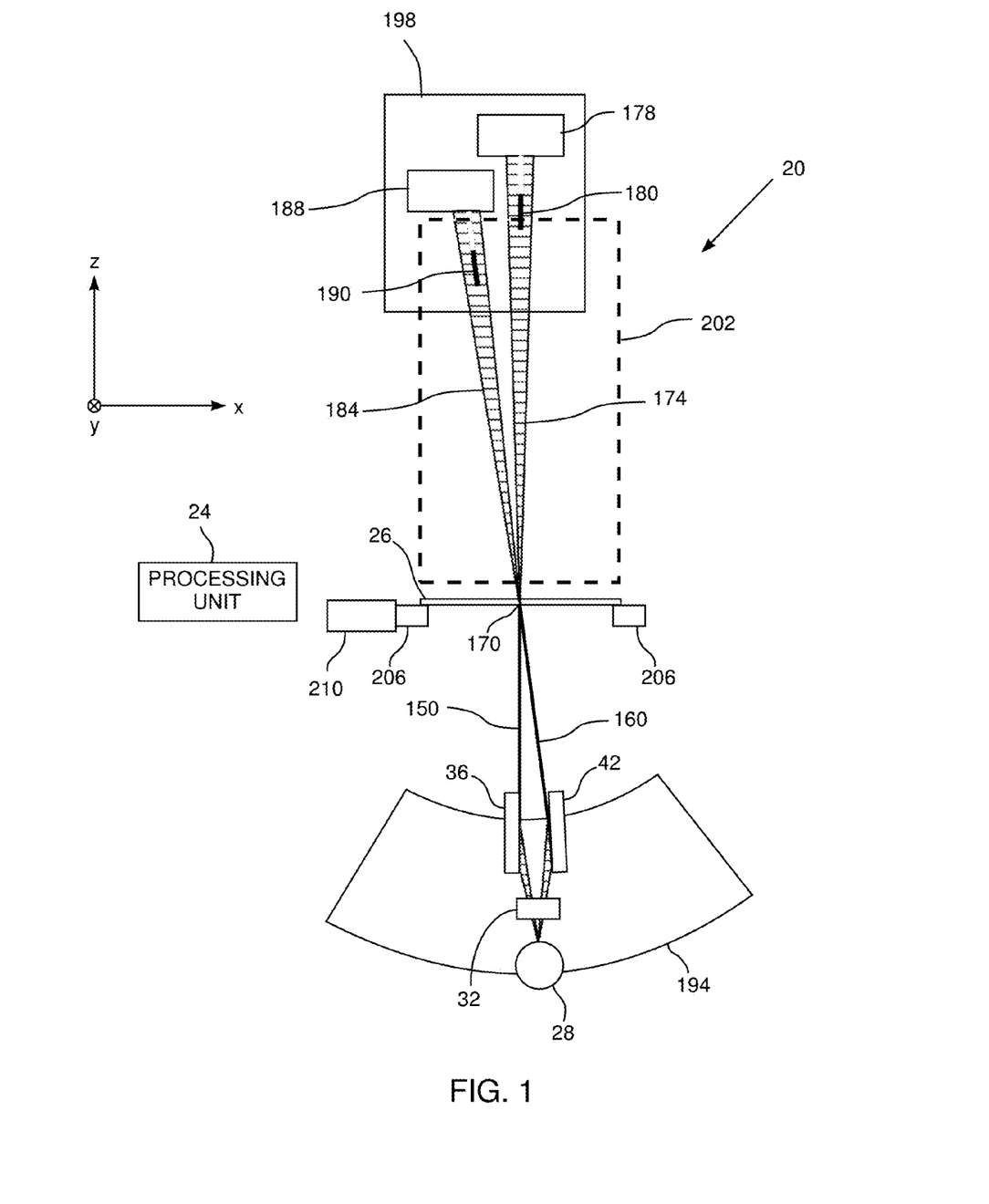
FIG. 1 is a schematic diagram of an X-ray scatterometry system, according to an embodiment of the present invention.

Reference is now made to FIG. 1, which is a schematic diagram of an X-ray scatterometry system 20, according to an embodiment of the present invention. System 20 is operated by a processing unit (PU) 24, which acts as a system processor and which uses software stored in a memory of the unit to operate system 20. The software may be downloaded to PU 24 in electronic form, over a network, for example, or it may, alternatively or additionally, be provided and/or stored on non-transitory tangible media, such as magnetic, optical, or electronic memory. PU 24 typically uses a graphic user interface (GUI) and an input device, such as a keypad or a pointing device, for the processing unit. A user of system 20 may provide input to the system, such as values of operating parameters for the system, as well as receiving results from the system, via the GUI and the input device.

System 20 is used to analyze physical characteristics of a macroscopically planar sample 26, such as a silicon wafer that has lithographically patterned features. Sample 26 is described in more detail below, and for clarity in the description herein the planar sample is assumed to define a three-dimensional set of axes, the sample lying in an xy plane of the axes and defining a z axis as perpendicular to the sample. The xy plane is typically horizontal, so that the sample is typically horizontal. However, it will be understood that the xy plane, and the sample, may be in any convenient orientation, and that the horizontal orientation is by way of example. The plane of the paper is assumed to lie in an xz plane.

System 20 comprises a micro-focus X-ray source 28, which is configured to produce beams of X-rays having wavelengths less than 0.1 nm. To produce these beams, the source is typically operated at approximately 50 kV, using a molybdenum, silver, or other suitable anode. The source may be implemented using a commercial micro-focus X-ray tube, such as is available, for example, from Oxford X-ray Technology Group, of Scotts Valley, Calif., or from rtw RÖNTGEN-TECHNIK DR. WARRIKHOFF GmbH & Co. KG, of Berlin, Germany.

The beams from source 28 traverse a shutter/slit assembly 32, comprising a shutter and one or more slits formed of X-ray opaque material, and which is under the overall control of PU 24. The shutter of assembly 32 prevents X-rays from source 28 exiting the assembly except as required by operation of system 20. PU 24 configures the one or more slits of assembly 32 so that two beams exit from the assembly. The slits direct each of the beams to beam conditioning assemblies 36 and 42, and the slits are arranged to adjust a respective divergence and spatial extent of each of the beams to corresponding with requirements of the beam conditioning assemblies.

Figure 2:
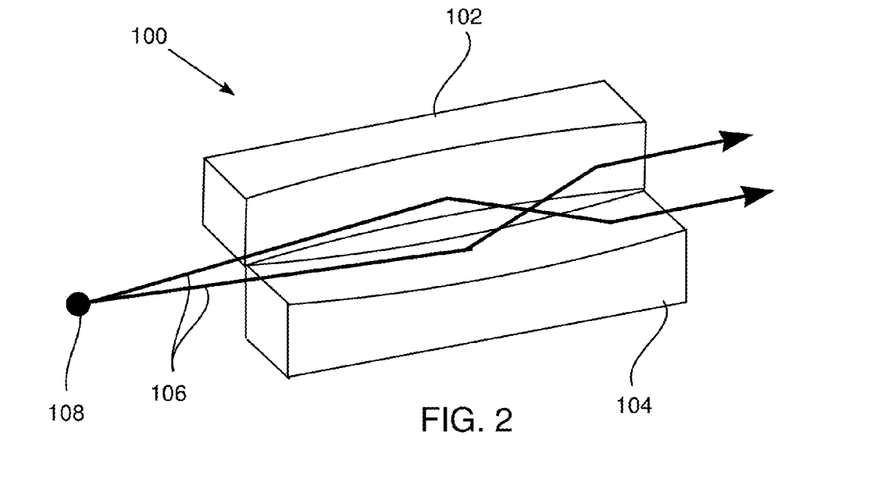
FIG. 2 is a schematic diagram illustrating an X-ray beam conditioning assembly, according to an embodiment of the present invention.

FIG. 2 is a schematic diagram illustrating an X-ray beam conditioning assembly 100, according to an embodiment of the present invention. Assembly 100 comprises two multi-layer mirrors 102, 104, which have reflecting surfaces as portions of elliptical or parabolic cylinders. The two mirrors are mounted side by side and orthogonal to each other. Such an arrangement, known as Montel optics, may be configured to focus an incoming X-ray beam 106 from a source 108, or to collimate the beam, or to produce a beam that is partly focused and partly collimated. Montel optics assemblies are available from Axo Dresden GmbH of Dresden, Germany. Alternate multilayer mirrors with higher efficiencies, such as the FOX 3D from Xenocs of Sassenage, France are also suitable.

Figure 3:
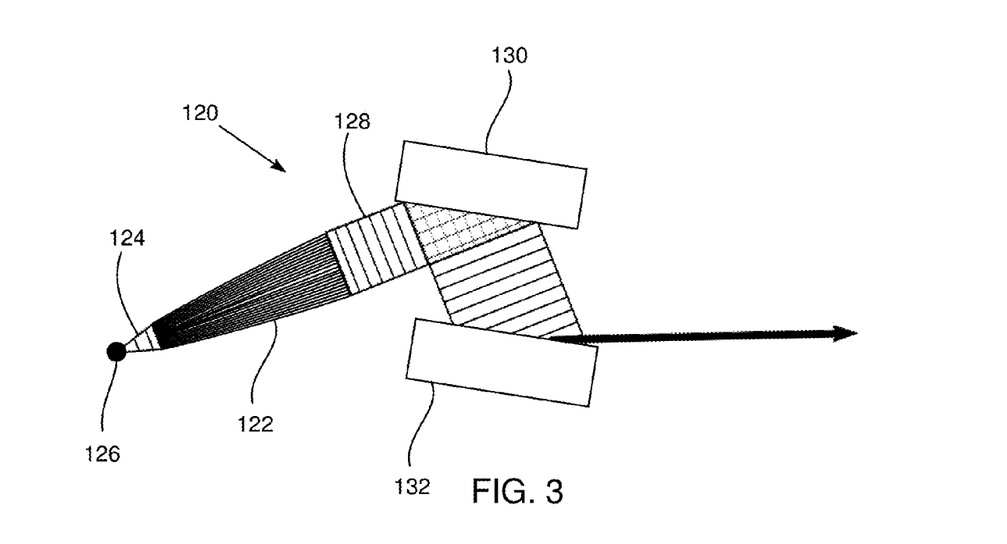
FIG. 3 is a schematic diagram illustrating an alternative X-ray beam conditioning assembly, according to an embodiment of the present invention.

FIG. 3 is a schematic diagram illustrating an alternative X-ray beam conditioning assembly 120, according to an embodiment of the present invention. Assembly 120 comprises a polycapillary collimating optic 122 which collects a diverging X-ray beam 124 from a source 126, and converts the beam to a quasi-parallel beam 128. Capillary optics such as optic 120 are available from XOS Corporation of East Greenbush, N.Y., and from the Institute for Scientific Instruments GmbH of Berlin, Germany. The quasi-parallel beam from optic 122 is directed to a first optic crystal element 130 and from there to a second optic crystal element 132. The two elements together form a composite monochromator and compression optic. The compression is achieved by diffracting from asymmetric planes in the crystals that are not parallel to the crystal faces. Elements 130 and 132 act as a dispersing element that spreads different wavelengths to different angles and the wavelengths may be selected downstream with a slit that selects a narrow range of the dispersed wavelengths. Both element 130 and element 132 may be configured from silicon or germanium single crystals, as is known in the art.

Returning to system 20 (FIG. 1), beam conditioning assemblies 36 and 42 may be configured as either assembly 100 or as assembly 120, or as any other suitable beam conditioning assembly known in the art. Assemblies 36 and produce respective beams 150 and 160, and the assemblies are configured to define respectively the exiting range of angles, i.e., the degree of collimation, the exiting range of wavelengths, i.e., the degree of monchromaticity, and the spatial extent of their respective exiting beams. The exiting beam characteristics, i.e., the collimation, monchromaticity, and extent of the exiting beam may typically be set by a user of system 20, by adjustment of the conditioning assemblies according to an intended use of the system. For example, if the system is to inspect a small region, the exiting beam may be configured to be collimated and of small spatial extent. Alternatively, if a large area is to be inspected, the exiting beam may be configured to be focused and to have a relatively large spatial extent. (Focusing the beam onto a system detector, described in more detail below, may increase the system resolution.)

Conditioning assemblies 36 and 42, and shutter/slit assembly 32, are configured so that beam 150 and beam 160 are both incident, with differing angles of incidence, on a common point 170 on sample 26.

Beam 150 is diffracted by features of a surface 172 of sample 26, to form a diffracted beam 174. For clarity, surface 172 is assumed to comprise a top surface of sample 26, but it will be understood that surface 172 may be either the top or bottom surface of the sample. The other surface of sample 26 is typically plane. The diffraction from surface 26 is accounted for in a model of the diffracted beam, described below. A first detector 178 is configured to receive diffracted beam 174, and a beam stop 180 is positioned in front of the detector to block directly transmitted X-rays from beam 150. I.e., beam stop 180, when subtended to point 170, is configured to have substantially the same angular range as incident beam 150, so as to block un-diffracted X-rays from sample 26.

Beam 160 is also diffracted by the features of surface 172, to form a diffracted beam 184. A second detector 188 is configured to receive diffracted beam 184, and a beam stop 190, having the same angular range as incident beam 160, is positioned in front of the detector to block directly transmitted X-rays from beam 160.

Beam stops 180 and 190 should be configured to produce minimal scatter, for example by being formed from thin slabs of single crystal silicon that have surfaces which have been asymmetrically cut, lapped, polished and etched.

Beam detectors 178 and 188 may be staggered in position so that even though there may only be a small separation of the two diffracted beams, both detectors are able to fully acquire the beams. The beam detectors may be two-dimensional (2D) or one-dimensional (1D), and should be capable of photon counting. The elements of the detectors should typically be sufficiently small so as to provide an angular acceptance of less than about 0.1 mrad, so that they are able to measure the small-angle scattering intensity distribution from sample 26 with good angular resolution.

Examples of suitable beam detectors include, but are not limited to, charge coupled device (CCD) and complementary metal oxide semiconductor (CMOS) cameras that are available commercially. Alternatively, the beam detectors may comprise silicon PIN diode array detectors, such as one of the Pilatus or Eiger series of devices manufactured by DECTRIS Ltd. of Baden, Switzerland.

In some embodiments the region between sample 26 and detectors 178 and 188 may include an evacuated chamber 202, typically a tubular chamber having X-ray transparent windows at its ends. The evacuated space within the chamber eliminates scatter of X-rays by air between the sample and the detectors.

Source 28, assembly 32, and conditioning assemblies 36 and 42 are mounted on a rotatable source-mount 194, also herein termed stage 194. The stage has an axis of rotation parallel to the y axis, is configured to rotate around point 170, and its rotation is controlled by PU 34. Thus, rotation of the stage rotates beams 150 and 160 about a line through point 170 and parallel to the y-axis.

Beam detectors 178 and 188, and beam stops 180 and 190, are mounted on a motorized detector-mount 198, herein also termed a stage 198. The motion of stage 198 is also controlled by PU 34, so that for any rotation of stage 194 beam stops 180 and 190 continue to block the direct X-ray beams, while detectors 178 and 188 continue to be able to acquire the diffracted beams, since the movement of stage 198 is configured to maintain detectors 178 and 188 in alignment with the diffracted beams. In some embodiments stage 198 is configured to rotate the beam stops and the detectors about an axis parallel to the y-axis through point 170.

Sample 26 is mounted on a sample-support 206, herein also termed chuck 206, which allows X-rays to be transmitted substantially over the surface of the sample. Typically, chuck 206 comprises a ring-like sample support but other designs are possible, such as a three-point kinematic mount for the sample. Chuck 206 is mounted on an xyφ-table 210, that is used to set the spatial position of the sample, in the xy plane, with respect to the incident X-ray beams. Table 210 is also configured to set the azimuth rotation φ of sample 26 about an axis perpendicular to the surface of the sample.

Figure 4:
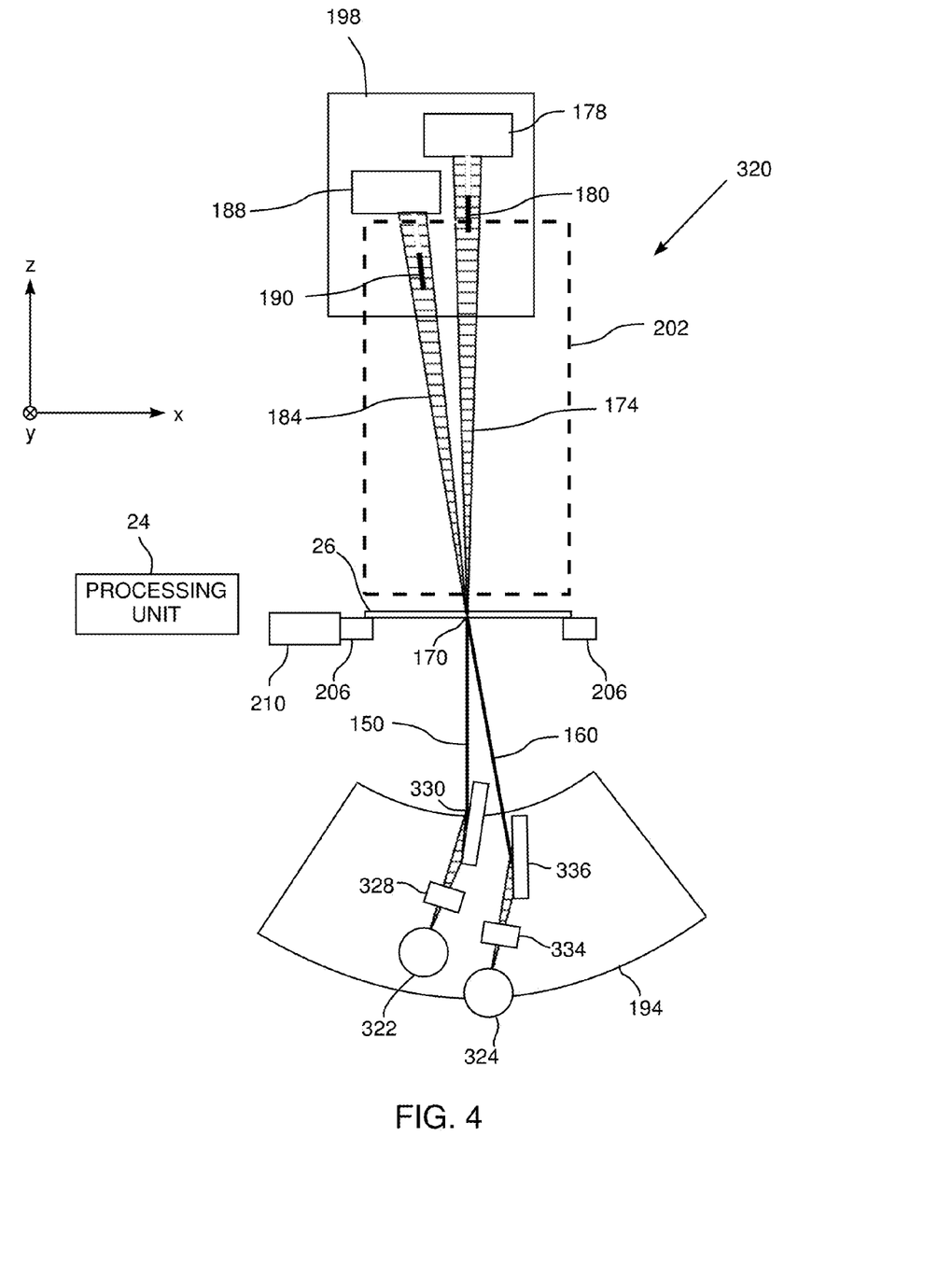
FIG. 4 is a schematic diagram of an X-ray scatterometry system, according to an alternative embodiment of the present invention.

FIG. 4 is a schematic diagram of an X-ray scatterometry system 320, according to an alternative embodiment of the present invention. Apart from the differences described below, the operation of system 320 is generally similar to that of system 20 (FIGS. 1, 2, and 3), and elements indicated by the same reference numerals in both systems 20 and 320 are generally similar in construction and in operation. In contrast to system 20, where beams 150 and 160 are produced by a single source, in system 320 there are two separate X-ray sources 322, 324, generally similar to X-ray source 28. Each source is configured to emit a single beam which is directed via a shutter/slit assembly to a beam conditioner. Thus source 322 directs its beam via a shutter/slit assembly 328 to a beam conditioning assembly 330, so as to produce beam 150. Similarly, source 324 directs its beam via a shutter/slit assembly 334 to a beam conditioning assembly 336, generally similar to assembly 36, so as to produce beam 160.

Sources 322, 324, assemblies 328, 330 and assemblies 334, 336 are all mounted on rotatable stage 194. As for system 20, in system 320 beams 150 and 160 are configured to meet at point 170 on sample 26, and rotation of the stage rotates the beams about a line through point 170 parallel to the y-axis.

While sources 322 and 324 are separate, the two sources may be configured to operate simultaneously. Thus, as for system 20, beams 150 and 170 are incident on point 170 at the same time.

Figure 5:
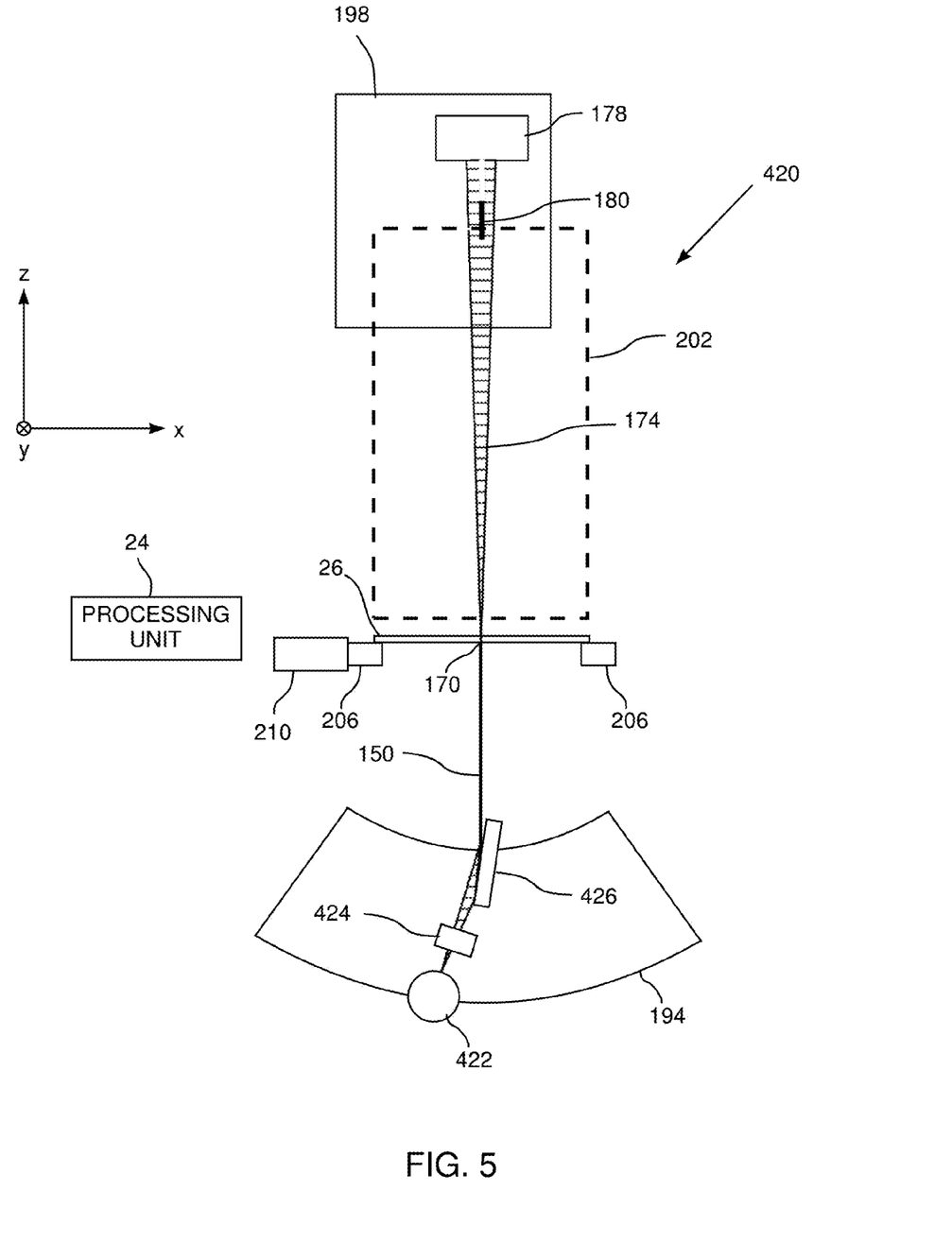
FIG. 5 is a schematic diagram of an X-ray scatterometry system, according to a further alternative embodiment of the present invention.

FIG. 5 is a schematic diagram of an X-ray scatterometry system 420, according to an alternative embodiment of the present invention. Apart from the differences described below, the operation of system 420 is generally similar to that of systems 20 and 320 (FIGS. 1-4), and elements indicated by the same reference numerals in systems 420, 320, and 20 are generally similar in construction and in operation. In contrast to systems 20 and 320, in system 420 only a single beam, beam 150, is generated at any given time. The single beam is generated by a single X-ray source 422. Source 422 directs its beam via a shutter/slit assembly 424 to a beam conditioning assembly 426, generally similar to assembly 36, so as to produce beam 150. Source 422, and assemblies 424, 426 are all mounted on rotatable stage 194.

Figure 6A:
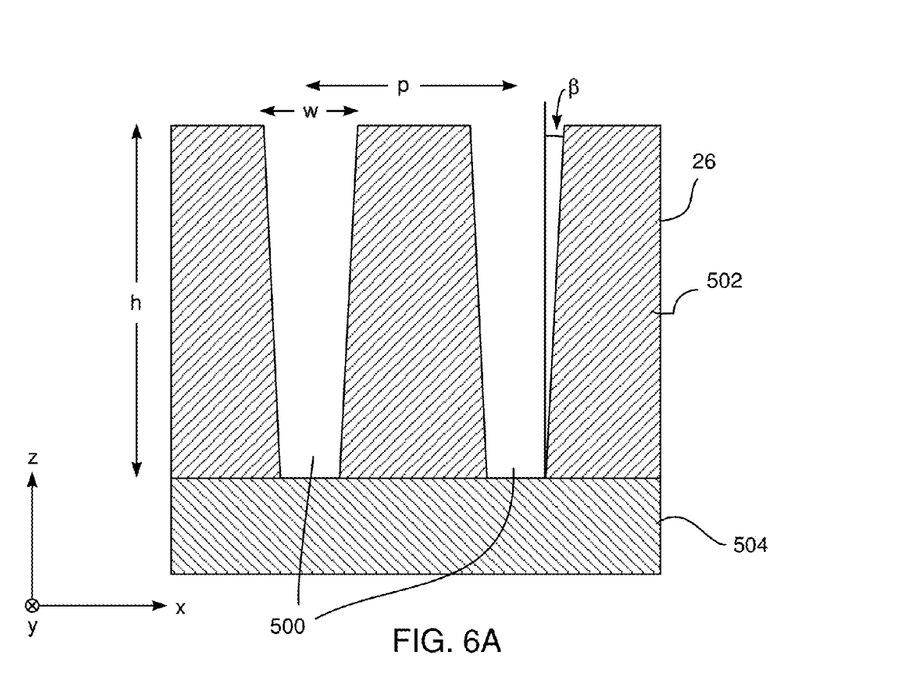
FIG. 6A is a schematic cross-section of a portion of a sample investigated in an X-ray scatterometry system, according to an embodiment of the present invention.

FIG. 6A is a schematic cross-section of a portion of sample 26, according to an embodiment of the present invention. Sample 26 is herein, by way of example, assumed to be formed with an array of one-dimensional (1D) trenches 500 that are parallel to the y-axis. Trenches 500 are assumed to be formed in a material 502, such as $SiO_2$, or materials covering a substrate 504, typically silicon, or the trenches may have been etched into substrate 504 itself. Each trench is assumed to have a height h, a width at top w, a sidewall angle (SWA) β i.e., the angle of the wall measured with respect to the z-axis. The trenches are separated in the x-direction by a pitch p.

Figure 6B:
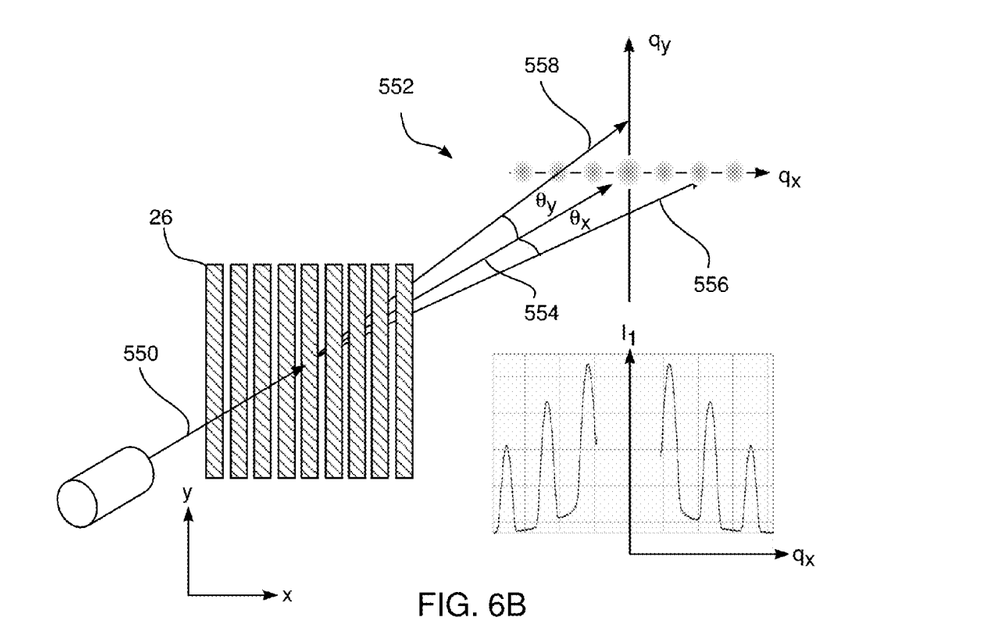
FIG. 6B is a schematic illustration of diffraction of X-rays by the sample of FIG. 6A, according to an embodiment of the present invention.

FIG. 6B is a schematic illustration of diffraction of X-rays by the sample of FIG. 6A, according to an embodiment of the present invention. An incident X-ray beam 550 impinges on sample 26, and the sample diffracts the incident beam. By way of example, three rays of a diffracted beam 552 are illustrated, a first ray 554 that is undeflected from beam 550, a second ray 556 that deflects from beam 550 in the x-direction by an angle $\theta_x$, and a third ray 558 that deflects from beam 550 in the y-direction by an angle $\theta_y$. In general, there are multiple rays in diffracted beam 552, each of the rays having a pair of values $(\theta_x, \theta_y)$ defining the deflection of the ray.

Diffracted beam 552 is incident on an X-ray detector, not shown in the diagram but herein assumed to be a detector comprising a two-dimensional array of pixel detectors such as detector 178 or 188. Embodiments of the present invention integrate the values of the signals generated by the pixels along the y-axis, to give sets of integrated signals, herein termed $I_1$, each integrated signal corresponding to a different x-value of the detector.

Rather than using x and y values to define a position of the diffracted beam on the detector, embodiments of the present invention use values of $q_x$, $q_y$, defined as follows:

$$q_x = (2\pi/\lambda)\sin(2\theta_x),$$

$$q_y = (2\pi/\lambda)\sin(2\theta_y)$$

where λ is the X-ray wavelength and $\theta_x$, $\theta_y$ are the scattering angles in the x and y directions.

FIG. 6B schematically shows a theoretical graph of the integrated signals $I_1$ vs. $q_x$ for a 1D set of trenches.

Figure 7A:
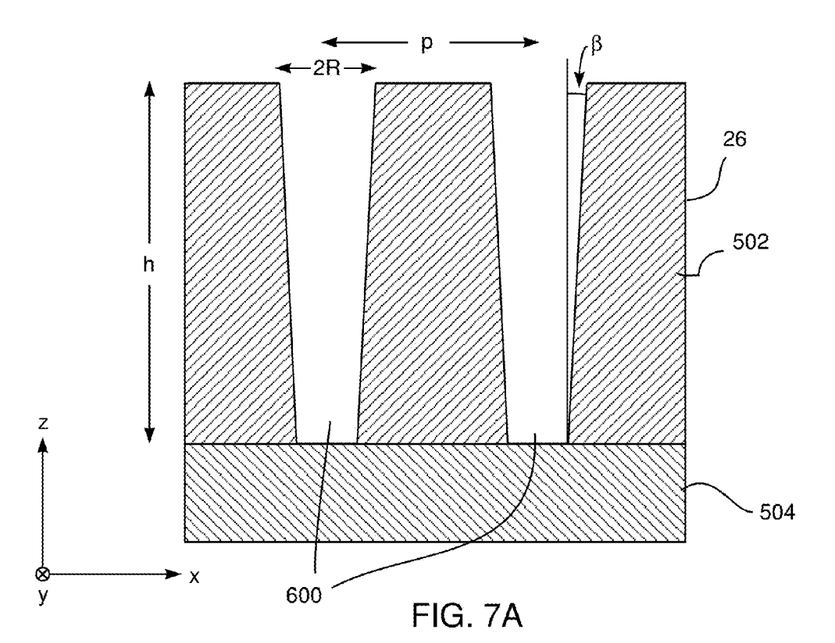
FIG. 7A is a schematic cross-section of a portion of an alternative sample investigated in an X-ray scatterometry system, according to an alternative embodiment of the present invention.
Figure 7B:
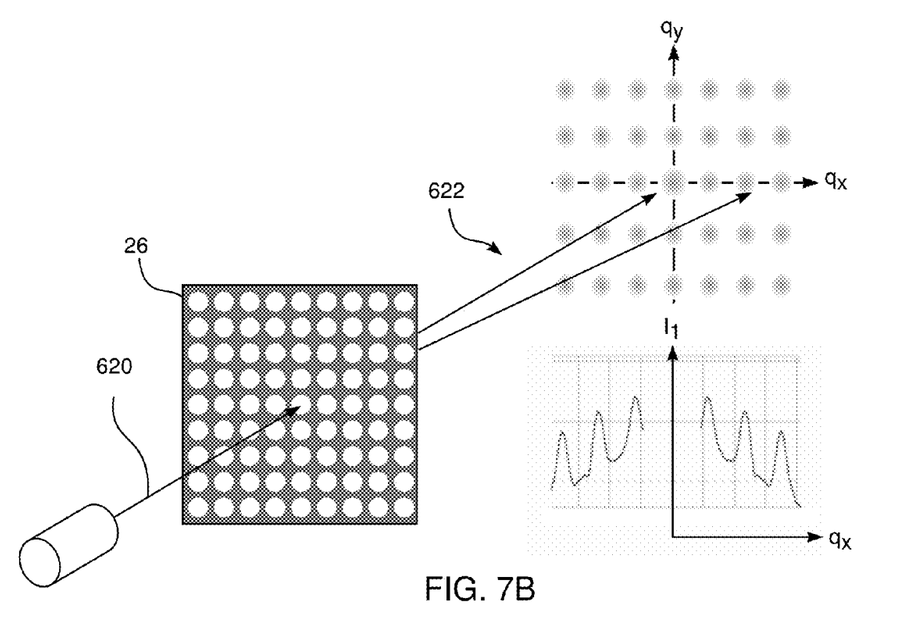
FIG. 7B is a schematic illustration of diffraction of X-rays by the sample of FIG. 7A, according to an embodiment of the present invention.

FIG. 7A is a schematic cross-section of a portion of sample 26, according to an alternative embodiment of the present invention. Sample 26 is now, by way of example, assumed to be formed of an array of two-dimensional (2D) cones 600 which are formed in material 502 covering substrate 504. The example described herein and illustrated in FIG. 7B shows a rectangular array of holes, but those of ordinary skill in the art will be able to generalize the arrays for other arrangements, such as hexagonal packing. Each cone is assumed to have a height h, a diameter at top 2R, a sidewall angle (SWA) β (corresponding to the semi-angle of the cone), and the cones are separated in the x-direction by a pitch p.

FIG. 7B is a schematic illustration of diffraction of X-rays by the sample of FIG. 7A, according to an embodiment of the present invention. An incident X-ray beam 620 impinges on sample 26, and the sample diffracts the incident beam to a diffracted beam 622.

Diffracted beam 622 is incident on an X-ray detector, herein assumed to be a two-dimensional array of pixel detectors substantially similar to that described above with reference to FIG. 6B. The values of the signals generated by the pixels are integrated along the y-axis, to give sets of integrated signals $I_1$, each integrated signal corresponding to a different x-value of the detector.

FIG. 7B schematically shows a theoretical graph of the integrated signals $I_1$ vs. $q_x$ for a 2D set of cones. (Expression $q_x$ is as described above with reference to FIG. 6B.)

Figure 8:
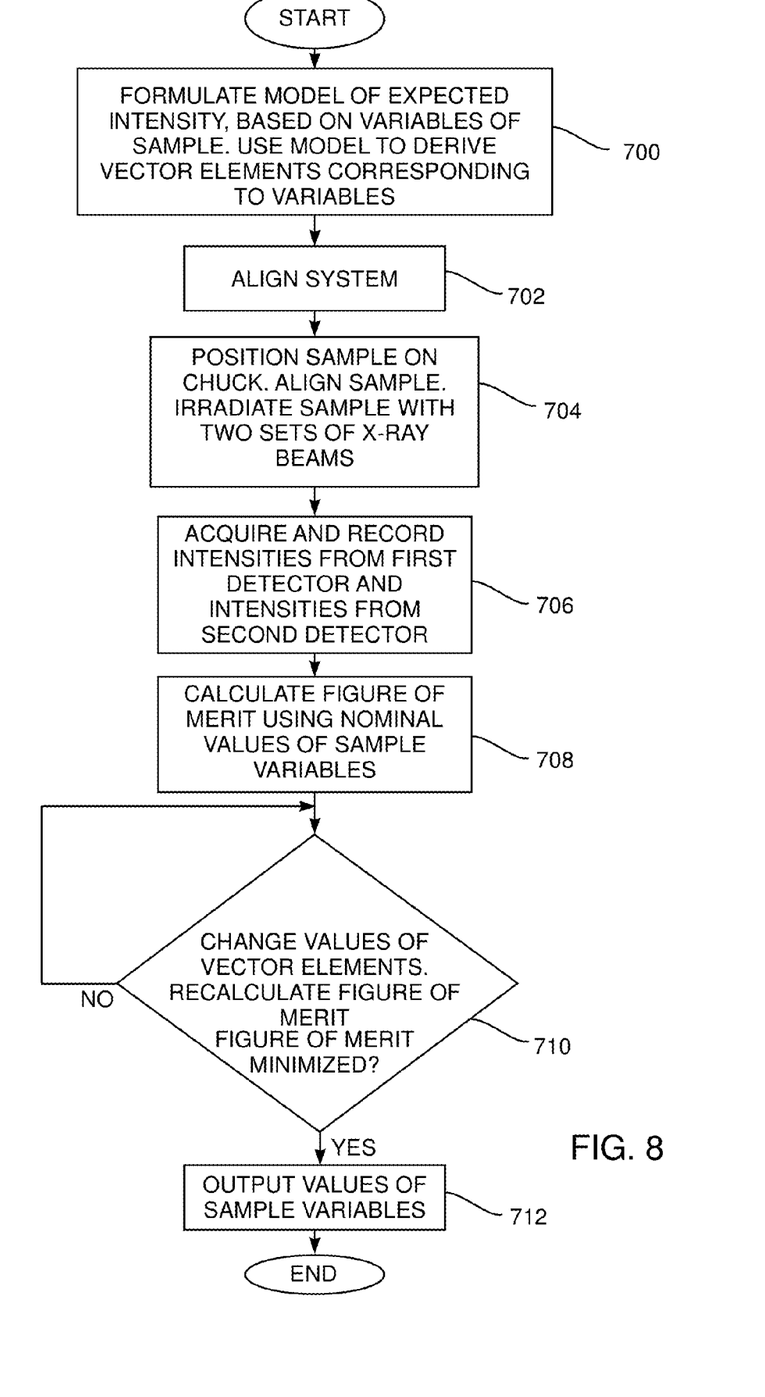
FIG. 8 is a flowchart of steps performed in operating an X-ray scatterometry system, according to an embodiment of the present invention.

FIG. 8 is a flowchart of steps performed in operating an X-ray scatterometry system, according to an embodiment of the present invention. For clarity, the description is directed to operating system 20, and to analyzing features of sample 26 with the system, and those having ordinary skill in the art will be able to adapt the description, mutatis mutandis, for other scatterometry systems, such as systems 320 and 420.

In a model formulation step 700, a vector comprising vector elements, corresponding to variables of sample 26 including geometric characterizations of surface 172 that are expected to affect the intensity of X-rays on the detectors, is formulated. The model, of the expected intensity on detectors 178, 188, is built from four components affecting the intensity. and each of the following four sections describes one of the components.

1. Theoretical X-Ray Intensity at a Detector

The geometric features of surface 172 cause the incoming X-ray beam to be diffracted. Two examples of geometric features are considered here.

a) In a first example surface 172 is formed of a set of one dimensional (1D) trenches, as described above with reference to FIGS. 6A, 6B, and the trenches have a height h, a width at top w, and a sidewall angle (SWA) β. In the analysis performed by PU 24, the profile of the trenches is approximated by considering the heights and widths of the trenches at m different positions, where m is the number of steps used in the approximation. In this case the mean height $h_i$ at the $i^{th}$ step is given by:

$$h_i = \frac{\frac{ih}{m} + \frac{(i-1)h}{m}}{2} = \left(\frac{2i-1}{2}\right) \cdot \Delta h \quad (1)$$

where $\Delta h = \frac{h}{m}$.

The mean width $w_i$ of the $i^{th}$ step is given by:

$$w_i = 2 \cdot \left(\frac{w}{2} - h_i \tan\beta\right) \quad (2)$$

The m different positions within the trenches act as m sets of linear slits, each set diffracting the incoming X-ray beam to give a multi-slit diffraction pattern, which is modulated by the single slit diffraction pattern generated by each of the slits. As stated above with regard to FIGS. 6A and 6B, signals on detectors 178 and 188 are integrated along their respective y axes. Equation (3) below gives an expression for the integrated signal acquired by each column (i.e., at a given y-value) of one of the detectors:

$$\int_{q_y} I(q_x, q_z) dq_y = \left(c_b(h_b/m)pN \frac{\sin(q_x pN/2)}{\sin(q_x p/2)}\right)^2 \times \qquad (3)$$

$$\left(\left[\sum_{i=1}^{m} w_i \frac{\sin(q_x w_i/2)}{q_x w_i/2} \cos(q_z h_i)\right]^2 + \left[\sum_{i=1}^{m} w_i \frac{\sin(q_x w_i/2)}{q_x w_i/2} \sin(q_z h_i)\right]^2\right) \times$$

$$\sum_{q_y} \left[\frac{\sin(q_y pN/2)}{q_y pN/2}\right]^2$$

where p, w, h, and $q_x$, $q_y$ are as defined above with reference to FIGS. 6A, 6B;

N is the number of illuminated trenches, so that pN is the width of the illuminated sample;

$c_b$ is a contrast factor indicative of the scattering contrast between the material in the trenches and their surroundings;

i=1, 2, . . . m; and $q_z = \omega \cdot q_x$, where $\omega$ is the angle between the incident X-ray beam and the normal to the surface of the sample.

b) In a second example surface 172 is formed of a set of two dimensional (2D) cones, as described above with reference to FIGS. 7A, 7B, and the cones have a height h, a diameter at top 2R, a sidewall angle β, and the cones are separated by a pitch p in the x-direction. PU 24 performs the same type of approximation as described above for the trenches, by considering the cones at m different positions.

Equation (1) above gives the mean height $h_i$ of the cones at the $i^{th}$ step of the approximation. Equation (4) below gives the mean radius $R_i$ of the cones at the $i^{th}$ step:

$$R_i = R - h_i \cdot \tan \beta \qquad (4)$$

The m different positions within the cones act as m arrays of 2D holes, each array diffracting the incoming X-ray beam to give a multi-hole diffraction pattern, which is modulated by the single hole diffraction pattern generated by each of the holes. As explained above, the signals on detectors 178 and 188 are integrated along their respective y axes. Equation (5) below gives an expression for the integrated signal acquired by each "y-column" of one of the detectors:

$$\int_{q_y} I(q_x) dq_y = \left\{2\pi c_c(h_c/m) \frac{\sin(q_x pN/2)}{\sin(q_x p)}\right\}^2 \times \qquad (5)$$

$$\sum_{q_y} \left\{\left[\frac{\sin(q_y pN/2)}{\sin(q_y p/2)}\right]^2\right\} \left\{\left[\sum_{i=1}^{m} R_i^2 \frac{J_1(R_i q)}{R_i q} \cos q_z h_i\right]^2 + \left[\sum_{i=1}^{m} R_i^2 \frac{J_1(R_i q)}{R_i q} \sin q_z h_i\right]^2\right\}$$

where $q = \sqrt{(q_x)^2 + (q_y)^2}$ (5B)

The variables in equations (5) and (5B) are as defined above for equation (3) and with reference to FIGS. 7A, 7B; in addition, $c_c$ is a contrast factor indicative of the scattering contrast between the material in the holes and their surroundings; and $J_1(\ )$ is a Bessel function.

2. X-Ray Intensity Modified by Roughness of the Diffracting Features

As stated above, and as shown in equations (3) and (5) the signals on detectors 178, 188 are integrated along the y-axis of the detectors. The integrated signal, corresponding in the examples above to the integrals generated by equations (3) or (5), is an integrated intensity (along the y-axis), and is herein rewritten as $I_1$.

Roughness of the features on sample 26 causes this intensity to be modified to an intensity $I_2$ according to equation (6):

$$I_2/I_1 \cdot \exp(-q_x^2 \sigma_r^2) \qquad (6)$$

where $\sigma_r$ corresponds to a Debye-Waller factor that characterizes the roughness and other random imperfections of the shape.

3. X-Ray Intensity Modified by Blurring

The expression for the intensity $I_2$ is correct for an incident parallel X-ray beam. In practice the incident beam has a finite angular divergence, causing blurring at the detector that is a function of an angular divergence of the beam, a cross-section of the beam at sample 26, and a finite size of the pixels of the detector. An expression for the blurred intensity $I_3(q)$ at a detector is given by equation (7):

$$I_3(q) = \sum_{i=-\frac{b}{2\Delta q}}^{\frac{b}{2\Delta q}} I_2(q + i\Delta q) * B(i\Delta q) \bigg/ \sum_{i=-\frac{b}{2\Delta q}}^{\frac{b}{2\Delta q}} B(i\Delta q) \qquad (7)$$

In equation (7), B(q) is a convolution given by:

$$B(q) = Rect \times Gauss = 0.5 * \{erf[(-q+\beta)/(\sqrt{2}\sigma)] - erf[(-q-\beta)/(\sqrt{2}\sigma)]\};$$

where σ is a standard deviation of the angular divergence of the beam, $$\beta = \frac{(s_{beam} + s_{pixel})}{2 \cdot f}$$

where $s_{beam}$ is the size of the beam, $s_{pixel}$ is the size of the pixels on the detector, and f is the distance between the sample and the detector.

In equation (7) $b = B_r \cdot B$, where $B_r$ is an integer, typically 5, $B = \sqrt{\beta^2 + Div^2}$, where Div=2.35σ; and Δq is a numerical integration step.

4. X-Ray Intensity Modified by Background Radiation

The intensity $I_3(q)$ of equation (7) does not take account of background radiation. An expression for the background intensity Bg, which is added to intensity $I_3(q)$, is given by equation (8):

$$Bg(q) = Bg_o + Bg_1(q - Bg_2)^{-Bg_3} \qquad (8)$$

where $B_{gn}$, n=0, . . . , 3 are fitted constants that describe the slowly varying function of q.

Thus, an expression for the integrated intensity I on a y-axis column of pixels of a detector is given by equation (9):

$$I = I_3(q) + Bg(q) \qquad (9)$$

It will be appreciated that the value of expression I depends on values of surface characteristics of sample 26, e.g., values of h, w, and β for the trenches of the example of FIGS. 6A and 6B, and values of h, R and β for the cones of the example of FIGS. 7A and 7B. The value of I also depends on other parameters, e.g., those used in sections (1)-(4) above.

In the following description, the expression for I is rewritten:

$$I = I(q_x, q_z; \vec{p}) \quad (10)$$

where $q_x$, $q_y$, are as defined above with reference to FIGS. 6A, 6B, and equation (3); and $\vec{p}$ is a multi-dimensional vector with vector elements corresponding to the parameters affecting the value of $I_f$.

The expression for I is used in a cost function, as is described below.

Returning to the flowchart, in an alignment step 702, elements of system 20 are aligned with each other, typically by initially positioning a calibration target on chuck 206, and operating source 28 while adjusting the positions of the system elements until acceptable signals are acquired by detectors 178 and 188. The calibration target may be a sample with periodic features that have typically been characterized by a method other than using system 20, for example by scanning electron microscopy. Alternatively, the calibration target may comprise a sample that has been previously analyzed by system 20.

In an initial operational step 704, a sample to be analyzed, typically a semiconducting wafer in a fabrication facility, is positioned on the chuck, and, once the sample has been aligned, it is irradiated with two beams of X-rays. If system 20 or system 320 is used, the two beams from source 28 or sources 322, 324 are typically simultaneous. If system 420 is used, the two beams from source 422 are sequential. The two beams irradiate the sample at different angles.

In a signal acquisition step 706, the intensities generated by the two beams are acquired by the detectors, and PU 24 records the corresponding signals generated by the detectors.

In an initial analysis step 708, PU 24 evaluates a figure of merit, FOM, for sample 26, according to the following equation:

$$FOM = \frac{w}{N}\sum_{i=1}^{N} [\log I_i - \log I(q_{x_i}, q_{z1}; \vec{p})]^2 + \frac{1-w}{M}\sum_{k=1}^{M} [\log I_k - \log I(q_{x_k}, q_{z2}; \vec{p})]^2 \quad (11)$$

where w is a weighting factor that is equal to 0.5 for the typical equal weighting of the two measurements, N is the number of irradiated pixels in the first detector, assumed to have an index 1, wherein the irradiating beam is at a first angle, and M is the number of irradiated pixels in the second detector, assumed to have an index 2, wherein the irradiating beam is at a second angle.

In equation (11) $I_i$, $I_k$, are the actual intensities measured respectively by the first and second detectors and $I(q_{x_i}, q_{z1}; \vec{p})$, $I(q_{x_k}, q_{z2}; \vec{p})$ are the expected intensities for a selected vector $\vec{p}$.

In step 708 the vector elements of $\vec{p}$ for the expressions providing the expected intensities, corresponding to the surface characteristics of sample 26, are typically chosen to correspond with the nominal values of the characteristics. E.g., for the example of the 1D trenches described above, the expected intensities are for sample 26 having values of, inter alia, the nominal height of the trenches, the nominal pitch of the trenches, and the nominal width at the top of the trenches.

PU 24 records the value of FOM found in step 708.

It will be understood that the difference between the logs of the two sets of values, in equation (11), operates as a cost function.

In a further analysis and comparison step 710 PU 24 iteratively changes the values of one or more of the vector elements of $\vec{p}$, reevaluates FOM, and records the new FOM values. The iterations continue until FOM is minimized.

In a final step 712, PU 24 outputs the values of the vector elements of $\vec{p}$ corresponding to the surface characteristics of sample 26, for the vector $\vec{p}$ at which FOM is a minimum.

In some embodiments, prior to final step 712, steps 704-710 are repeated after source-mount 194 has been rotated, and detector-mount 198 has been moved to maintain the alignment of the detectors. In this case PU 24 uses the new signals acquired in step 706 to reevaluate FOM.

The above description has, by way of example, considered samples with 1D trenches and 2D cones. It will be understood that embodiments of the present invention are not limited to determining profiles of sample surfaces comprising trenches and/or cones such as those described above. For example, the sample surface may comprise pillars, and/or trenches or cones having cross-sections with curved edges. Such embodiments may be analyzed by generating an appropriate vector $\vec{p}$. In general, substantially any profile may be determined by generating a corresponding vector $\vec{p}$.

While the description above has generally assumed that the samples referred to above have a horizontal orientation, and that the rotation axis of the source-mount is horizontal, it will be understood that these orientations are by way of example, and that the sample and/or the rotation axis may be in any convenient orientations including non-horizontal orientations.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. Apparatus, comprising:
   a sample-support, configured to fixedly retain a sample in a plane comprising an axis, the plane defining first and second regions in space that are separated by the plane;
   a source-mount, positioned in the first region, and configured to rotate about the axis;
   an X-ray source positioned in the first region on the source-mount and configured to direct first and second incident beams of X-rays to impinge simultaneously on a common point on the sample at respective first and second angles along respective beam axes that are orthogonal to the axis;
   a detector-mount positioned in the second region and configured to move in a plane orthogonal to the axis;
   an X-ray detector positioned in the second region on the detector-mount and configured to receive first and second scattered beams of X-rays transmitted through the sample in response to the first and second incident beams, and to output first and second signals, respectively, in response to the received first and second scattered beams; and a processor, configured to analyze the first and the second signals so as to determine a profile of a surface of the sample.

2. The apparatus according to claim 1, wherein the X-ray source comprises a single X-ray source configured to produce the first and second incident beams simultaneously.

3. The apparatus according to claim 1, wherein the X-ray source comprises a first X-ray source configured to produce the first incident beam and a second X-ray source configured to produce the second incident beam simultaneously with the first incident beam.

4. The apparatus according to claim 1, wherein the X-ray detector comprises a first detector located at a first position on the detector-mount so as to receive the first scattered beam and a second detector located at a second position on the detector-mount so as to receive the second scattered beam.

5. The apparatus according to claim 1, wherein the detector-mount is configured to move so as to maintain alignment of the X-ray detector with the first and second scattered beams on rotation of the source-mount about the axis.

6. The apparatus according to claim 5, wherein the detector-mount is configured to rotate about the axis.

7. The apparatus according to claim 1, wherein the processor is configured to formulate an expected first signal and an expected second signal for the X-ray detector in response to a theoretical profile of the surface, and to compare, using a cost function, the expected first and second signals with the outputted first and second signals so as to determine the profile.

8. The apparatus according to claim 7, wherein the processor is configured to minimize a sum of a first result of the cost function applied to the outputted first signal and the expected first signal and a second result of the cost function applied to the outputted second signal and the expected second signal so as to determine the profile.

9. The apparatus according to claim 1, wherein the plane is horizontal.

10. The apparatus according to claim 9, wherein the first region is below the sample, and wherein the second region is above the sample.

11. A method, comprising:
configuring a sample-support to fixedly retain a sample in a plane comprising an axis, the plane defining first and second regions in space that are separated by the plane;
positioning a source-mount, configured to rotate about the axis, in the first region;
positioning an X-ray source in the first region on the source-mount;
directing first and second incident beams of X-rays from the X-ray source to impinge simultaneously on a common point on the sample at respective first and second angles along respective beam axes that are orthogonal to the axis;

positioning a detector-mount, configured to move in a plane orthogonal to the axis, in the second region;
positioning an X-ray detector, configured to receive first and second scattered beams of X-rays transmitted through the sample in response to the first and second incident beams, in the second region on the detector-mount;
outputting first and second signals, respectively, in response to the received first and second scattered beams; and
analyzing the first and the second signals so as to determine a profile of a surface of the sample.

12. The method according to claim 11, wherein the X-ray source comprises a single X-ray source configured to produce the first and second incident beams simultaneously.

13. The method according to claim 11, wherein the X-ray source comprises a first X-ray source configured to produce the first incident beam and a second X-ray source configured to produce the second incident beam simultaneously with the first incident beam.

14. The method according to claim 11, wherein the X-ray detector comprises a first detector located at a first position on the detector-mount so as to receive the first scattered beam and a second detector located at a second position on the detector-mount so as to receive the second scattered beam.

15. The method according to claim 11, wherein the detector-mount is configured to move so as to maintain alignment of the X-ray detector with the first and second scattered beams on rotation of the source-mount about the axis.

16. The method according to claim 15, wherein the detector-mount is configured to rotate about the axis.

17. The method according to claim 11, wherein analyzing the first and the second signals comprises formulating an expected first signal and an expected second signal for the X-ray detector in response to a theoretical profile of the surface, and comparing, using a cost function, the expected first and second signals with the outputted first and second signals so as to determine the profile.

18. The method according to claim 17, and comprising minimizing a sum of a first result of the cost function applied to the outputted first signal and the expected first signal and a second result of the cost function applied to the outputted second signal and the expected second signal so as to determine the profile.

19. The method according to claim 11, wherein the plane is horizontal.

20. The method according to claim 19, wherein the first region is below the sample, and wherein the second region is above the sample.

* * * * *